US007390525B2

(12) United States Patent
Epstein et al.

(10) Patent No.: US 7,390,525 B2
(45) Date of Patent: *Jun. 24, 2008

(54) PROCESSES FOR PRODUCING POLYMER COATINGS FOR RELEASE OF THERAPEUTIC AGENT

(75) Inventors: Samuel J. Epstein, Newton, MA (US); Wendy Naimark, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 471 days.

This patent is subject to a terminal disclaimer.

(21) Appl. No.: 11/033,918

(22) Filed: Jan. 12, 2005

(65) Prior Publication Data

US 2005/0158359 A1    Jul. 21, 2005

Related U.S. Application Data

(63) Continuation of application No. 10/430,165, filed on May 6, 2003, now Pat. No. 6,923,996.

(51) Int. Cl.
*B05D 3/00* (2006.01)

(52) U.S. Cl. ............... 427/2.24; 427/2.26; 427/2.28; 427/2.3; 427/407.1; 427/409; 427/413; 427/421

(58) Field of Classification Search ............. 427/2.24, 427/2.26, 2.28, 2.3, 407.1, 409, 413, 421
See application file for complete search history.

(56) References Cited

U.S. PATENT DOCUMENTS 4,806,355 A   2/1989   Goosen et al. ............. 424/424

5,451,422 A   9/1995   Cain et al. .................. 426/602
5,660,873 A   8/1997   Nikolaychik et al. ....... 427/2.24

(Continued)

FOREIGN PATENT DOCUMENTS

EP   0623354 A1   11/1994

(Continued)

OTHER PUBLICATIONS

H.J. Larsen et al., "Cropping Reliability: Methods to Enhance Bud Survival and Cropping Reliability in Fruit Crops," WCRC 2000 Annual Report.

(Continued)

*Primary Examiner*—Bret Chen
(74) *Attorney, Agent, or Firm*—Mayer & Williams PC; David B. Bonham, Esq.; Keum J. Park, Esq.

(57) ABSTRACT

A method for furnishing a therapeutic-agent-containing medical device is provided. The method comprises: (a) providing a reactive layer comprising a cross-linking agent on a medical device surface; and (b) subsequently applying a polymer-containing layer, which comprises a polymer and a therapeutic agent, over the reactive layer. The cross-linking agent interacts with the polymer to form a cross-linked polymeric region that comprises the therapeutic agent. Moreover, in certain embodiments, the polymer-containing layer does not comprise the cross-linking agent at the time the polymer-containing layer is applied over the reactive layer. Examples of medical devices include implantable or insertable medical devices, for example, catheters, balloon, cerebral aneurysm filler coils, arterio-venous shunts and stents.

26 Claims, 1 Drawing Sheet

U.S. PATENT DOCUMENTS

| | | |
|---|---|---|
| 5,773,577 A | 6/1998 | Cappello .................... 530/350 |
| 5,820,918 A | 10/1998 | Ronan et al. ................. 427/2.1 |
| 5,837,313 A | 11/1998 | Ding et al. ................. 427/2.21 |
| 5,843,089 A | 12/1998 | Sahatjian et al. ............ 606/108 |
| 5,849,368 A | 12/1998 | Hostettler et al. ........... 427/536 |
| 5,879,697 A | 3/1999 | Ding et al. ................. 424/422 |
| 6,030,656 A | 2/2000 | Hostettler et al. ............ 427/2.3 |
| 6,048,620 A | 4/2000 | Zhong ..................... 428/424.4 |
| 6,096,018 A | 8/2000 | Luzio et al. ................. 604/500 |
| 6,120,904 A | 9/2000 | Hostettler et al. ........ 428/423.3 |
| 6,184,266 B1 | 2/2001 | Ronan et al. ................. 523/113 |
| 6,197,051 B1 | 3/2001 | Zhong ....................... 623/1.46 |
| 6,207,218 B1 | 3/2001 | Layrolle et al. ............ 427/2.27 |
| 6,228,845 B1 | 5/2001 | Donovan et al. .............. 514/44 |
| 6,231,600 B1 | 5/2001 | Zhong ....................... 623/1.42 |
| 6,270,902 B1 | 8/2001 | Tedeschi et al. .......... 428/423.1 |
| 6,287,285 B1 | 9/2001 | Michal et al. ............... 604/264 |
| 6,309,380 B1 | 10/2001 | Larson et al. ............... 604/502 |
| 6,316,018 B1 | 11/2001 | Ding et al. .................. 424/423 |
| 6,335,029 B1 | 1/2002 | Kamath et al. .............. 424/423 |
| 6,344,028 B1 | 2/2002 | Barry ..................... 604/96.01 |
| 6,368,356 B1 | 4/2002 | Zhong et al. ............. 623/23.75 |
| 6,517,888 B1 | 2/2003 | Weber ....................... 427/2.24 |
| 6,596,401 B1 | 7/2003 | Terry et al. .................. 428/447 |
| 6,923,996 B2 * | 8/2005 | Epstein et al. ............. 427/2.24 |

FOREIGN PATENT DOCUMENTS

| | | |
|---|---|---|
| GB | 2153235 A | 8/1985 |
| WO | WO 96/32907 | 10/1996 |
| WO | WO 02/058753 A2 | 8/2002 |
| WO | WO 02/058753 A3 | 8/2002 |
| WO | WO 03/084583 | 10/2003 |
| WO | WO 04/000267 A1 | 12/2003 |
| WO | WO 2004/060427 A1 | 7/2004 |

OTHER PUBLICATIONS

Jeremy M. Van Raamsdonk, "Towards Stronger Microcapsules for Non-Autologous Somatic Gene Therapy," Presented at INABIS '98—5$^{th}$ Internet World Congress on Biomedical Sciences at McMaster University, Canada, Dec. 7$^{th}$-16th.

Alginates for Pharmaceutical Applications. International Specialty Products, 1999, 4 pp.

* cited by examiner

PROCESSES FOR PRODUCING POLYMER COATINGS FOR RELEASE OF THERAPEUTIC AGENT

This is a continuation of U.S. patent application Ser. No. 10/430,165, filed May 6, 2003, now U.S. Pat. No. 6,923,996, and entitled "Processes for producing polymer coatings for release of therapeutic agent," which is incorporated by reference in its entirety herein.

BACKGROUND OF THE INVENTION

1. Field of the Invention

The present invention relates to medical devices with polymeric coatings and more particularly to medical devices having polymer coatings that release therapeutic agent.

2. Brief Description of the Background Art

Numerous medical devices have been developed for the delivery of therapeutic agents to the body. For example, in accordance with some delivery strategies, a therapeutic agent is provided within a polymeric carrier layer that is associated with a medical device. Once the medical device is placed at the desired location within a patient, the therapeutic agent is released from the medical device. The desired release profile for the therapeutic agent is dependent upon the particular treatment at hand, including the specific condition being treated/prevented, the specific therapeutic agent selected, the specific site of administration, and so forth.

Therapeutic agents are frequently handled in aqueous solutions. Unfortunately, directly coating the surface of a metallic medical device, for example, a stent, with an aqueous solution can be problematic, because metals are typically quite hydrophobic. As a result, the cohesive forces within the aqueous solution tend to pool the solution on the medical device surface, rather than wetting the entire surface. Low coating retention, frequently involving very expensive therapeutic agents, is associated with this phenomenon.

SUMMARY OF THE INVENTION

The above and other issues are addressed by the present invention, in which a novel method is provided for producing a therapeutic agent releasing medical device.

According one embodiment of the present invention, a reactive layer comprising a cross-linking agent is initially provided on a medical device surface. Subsequently, a polymer-containing layer comprising a polymer and a therapeutic agent is applied over the reactive layer. Once the two layers have been established, the cross-linking agent from said reactive layer is free to interact with the polymer in the polymer-containing layer, forming a cross-linked polymeric region that contains the therapeutic agent.

Examples of medical devices include implantable or insertable medical devices, for example, catheters, balloons, cerebral aneurysm filler coils, arterio-venous shunts and stents.

One advantage of the present invention is that a process is provided, which allows for the controlled manufacture of a therapeutic-containing polymer layer on a medical device surface.

Another advantage of the present invention is that a process is provided, which allows a hydrophobic medical device surface, such as a metallic surface, to be effectively wetted by an aqueous, or otherwise hydrophilic solution, containing a therapeutic agent, minimizing pooling or beading of the solution.

Still another advantage of the present invention is that a coating is provided, which protects the therapeutic agent from rapid release during medical device deployment and also controls release of the therapeutic agent to the target location after deployment.

The above and other embodiments and advantages of the present invention will be readily understood by those of ordinary skill in the art upon review of the Detailed Description and Claims to follow.

DETAILED DESCRIPTION OF THE INVENTION

Figure 1:
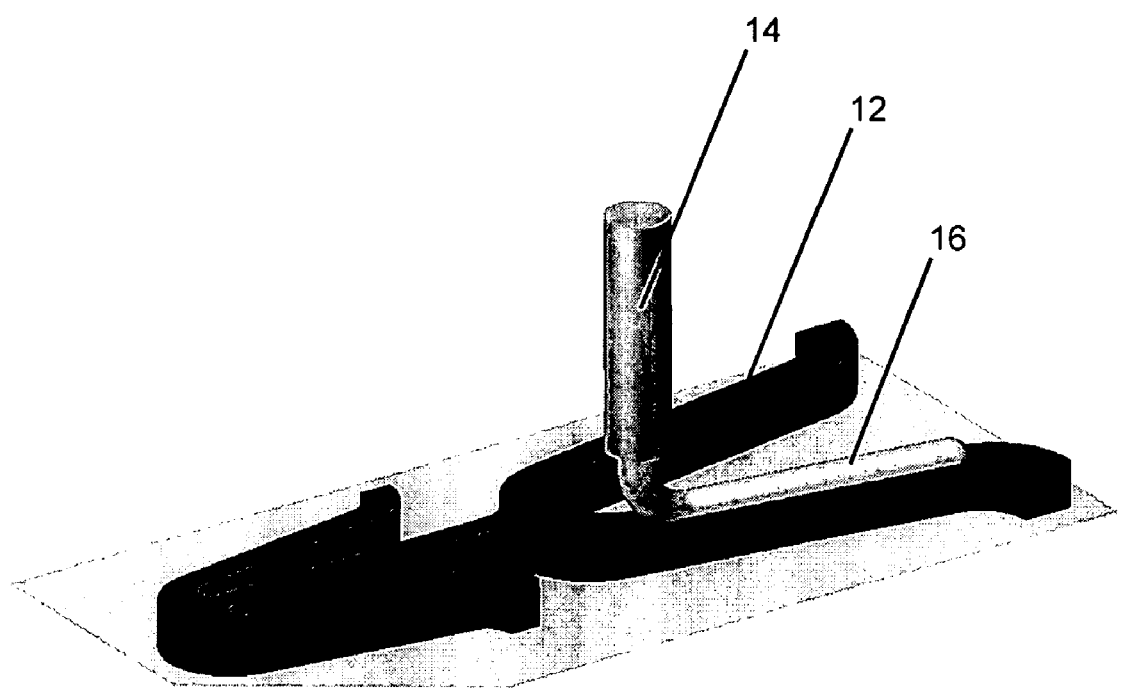
FIG. 1 is a schematic perspective view illustrating a stereolithographic deposition technique, in accordance with an embodiment of the present invention.

In accordance with the present invention, a variety of methods are described below for providing therapeutic-agent-releasing polymer coatings on medical device surfaces. These methods generally comprise the following steps: (a) providing a medical device having on its surface a reactive layer comprising a cross-linking agent; and (b) applying a polymer-containing layer, which comprises a polymer and a therapeutic agent, over the reactive layer. Once the polymer-containing layer is applied, the cross-linking agent from the reactive layer interacts with the polymer species from the polymer-containing layer to form a cross-linked polymeric region. The cross-linked polymeric region contains the therapeutic agent, and can be referred to as a matrix layer or a carrier layer.

Once formed, the cross-linked polymeric region typically (a) acts to retain therapeutic agent during device deployment and (b) releases therapeutic agent in a controlled manner subsequent to device deployment. The use of in situ polymerization reduces the need to handle highly viscous polymer solutions that contain therapeutic agents.

Preferred medical devices for use in conjunction with the present invention are implantable or insertable medical devices, including catheters (for example, urinary catheters or vascular catheters such as balloon catheters), guide wires, balloons, filters (e.g., vena cava filters), stents (including coronary vascular stents, cerebral stents, urethral stents, ureteral stents, biliary stents, tracheal stents, gastrointestinal stents and esophageal stents), stent grafts, cerebral aneurysm filler coils (including GDC—Guglilmi detachable coils—and metal coils), vascular grafts, myocardial plugs, patches, pacemakers and pacemaker leads, heart valves, and biopsy devices; indeed, any substrate (which can be, for example, metallic, polymeric or ceramic, preferably metallic) which is coated in accordance with the present invention and which is designed for use in a patient, either for procedural use or as an implant.

The medical devices for use in connection with the present invention include drug delivery medical devices for systemic treatment or for treatment of any mammalian tissue or organ. As used herein, "treatment" refers the prevention of a disease or condition, the reduction or elimination of symptoms associated with a disease or condition, or the substantial or complete elimination a disease or condition. Preferred subjects are mammalian subjects and more preferably human subjects. Non-limiting examples of tissues and organs for treatment include the heart, coronary or peripheral vascular system, lungs, trachea, esophagus, brain, liver, kidney, bladder, urethra and ureters, eye, intestines, stomach, colon, pancreas, ovary, prostate, gastrointestinal tract, biliary tract, urinary tract, skeletal muscle, smooth muscle, breast, cartilage and bone.

As previously indicated, in accordance with various embodiments of the present invention, a process is provided that comprises: (a) providing a medical device having on its surface a reactive layer that comprises a cross-linking agent; and (b) applying, over the reactive layer, a polymer-containing layer comprising (i) a polymer that is crosslinked by the crosslinking agent and (ii) a therapeutic agent. After the polymer-containing layer is established over the reactive layer, the crosslinking agent and the polymer associate with one another, for example, as a result of diffusion and/or any other mass-transport mechanism, leading to crosslinking of the polymer species. The reactive layer and the polymer-containing layer are preferably sufficiently reactive with one another to lead to crosslinking of essentially all of the polymer within the polymer-containing layer by the crosslinking agent.

A "polymer" is any macromolecule composed of two or more monomers, and includes dimers, trimers, tetramers, etc. A "monomer" is a polymerizable molecule. Typically, the polymers of the present invention will have a median number of monomers that numbers in the tens (10 to 99), hundreds (100 to 999), thousands (1000 to 9999), tens of thousands (10,000 to 99,999) or more.

A "cross-linking agent" is any species that is capable of linking a first polymer chain to a second polymer chain. Linking can be covalent or non-covalent (e.g., ionic). In some instances, at least a portion of the crosslinking agent becomes incorporated into the crosslinked composition.

Crosslinkable polymers for use in connection with the present invention may be crosslinked using either non-ionic crosslinking (e.g., covalent crosslinking) or ionic crosslinking.

Crosslinkable polymers suitable for the practice of the present invention include carboxylic, sulfate, hydroxy and amine-functionalized polymers, among others. Suitable crosslinkable polymers which may be used in the practice of the present invention include homopolymers, copolymers and polymer blends comprising one or more of the following: polyhydroxy ethyl methacrylate, polyvinyl alcohol, polyacrylamide, poly (N-vinyl pyrrolidone), polyethylene oxide, hydrolyzed polyacrylonitrile, polyacrylic acid, polymethacrylic acid, polyethylene amine, alginic acid, pectinic acid, carboxy methyl cellulose, hyaluronic acid, heparin, heparin sulfate, chitosan, carboxymethyl chitosan, chitin, pullulan, gellan, xanthan, carboxymethyl starch, carboxymethyl dextran, chondroitin sulfate, cationic guar, potassium polymetaphosphates (e.g., Kurrol salts), cationic starch, as well as acid salts and esters thereof where appropriate.

Ionic crosslinking agents may be in the form of anions or cations, depending on whether the polymer to be crosslinked is cationically or anionically crosslinkable.

Appropriate cationic crosslinking agents include alkaline earth metals, such as calcium, magnesium, barium, strontium, and beryllium ions; transition metals, such as iron, manganese, copper, cobalt, zinc, and silver ions; other metallic elements, such as boron, aluminum, lead, and bismuth ions; and polyamonium ions, such as $^+H_3N-(-H_2)_n-NH_3^+$ or $^+H_3N-(CH_2)_n-CH((CH_2)_m-NH_3^+)((CH_2)_p-NH_3^+)$ where n is an integer ranging from 1 to 8, and m and p are integers ranging from 0 to 8. Preferred cationic crosslinking agents are calcium and barium ions.

Anionic crosslinking agents appropriate for the practice of the present invention include those derived from polybasic organic or inorganic acids. Appropriate anionic crosslinking agents include phosphate, sulfate, citrate, borate, succinate, maleate, adipate, and oxalate ions.

One preferred embodiment of the present invention utilizes the following: (a) a reactive layer comprising a multivalent cationic crosslinking agent (e.g., calcium or barium) and (b) a polymer-containing layer comprising (i) one or more monovalent salts of alginic acid (e.g., sodium alginate and/or potassium alginate) and (ii) a therapeutic agent. In this embodiment, upon application of the polymer-containing layer over the reactive layer, the divalent cations from the reactive layer interact with the alginate polymers from the polymer-containing layer, in the presence of the therapeutic agent, resulting in the formation of a cross-linked, therapeutic-agent-containing matrix.

Ionically crosslinked systems are particularly advantageous when used in connection with medical devices having hydrophobic surfaces. This is because the salts that are typically used to provide the cationic or anionic crosslinking agent also act to reduce the surface tension of the solution (generally aqueous) that is applied to the hydrophobic surface. As a result, coating retention is increased. Moreover, such salts are typically inexpensive as compared to the therapeutic agent that is found in the polymer-containing layer. By establishing a relatively hydrophilic, salt-containing layer upon the device surface, retention of the subsequently applied polymer-containing layer, and hence retention of therapeutic agent, is improved. Furthermore, such crosslinking agents are frequently of low molecular weight, and hence of high mobility, enhancing interactions between the crosslinking agent and the polymer.

Preferred non-ionic crosslinking agents are those that react with groups present in the polymer such that covalent bonds are formed between different polymer chains. Suitable non-ionic crosslinking agents are polyfunctional compounds having at least two functional groups reactive with one or more functional groups present in the polymer(s). Exemplary crosslinking agents contain one or more of the following: carboxy groups, hydroxy groups, epoxy groups, halogen groups amino functional groups, or hydrogen unsaturated groups, which are capable of undergoing facile nucleophilic or condensation reactions with groups present in the polymer at temperatures up to about 100° C. Suitable crosslinking reagents include polycarboxylic acids or anhydrides; polyamines; epihalohydrins; diepoxides; dialdehydes (e.g., glutaraldehyde); diols; carboxylic acid halides, ketones and like compounds.

Other exemplary crosslinkable polymers for the practice of the present invention include polymers that contain amino acids (e.g., proteins), which can be covalently crosslinked to one another using an appropriate crosslinking agent. For example, the polymer-containing layer can comprise either (a) a polymer containing both lysine and glutamine or (b) a polymer containing lysine and a polymer containing glutamine. A corresponding crosslinking agent appropriate for use in this reactive layer is a transglutaminase enzyme. Upon application of the polymer-containing layer to the reactive layer, the transglutaminase enzyme from the reactive layer acts to covalently bond the glutamine and lysine within the polymer(s) in the presence of the therapeutic agent, forming a cross-linked therapeutic-agent-containing matrix.

The reactive layer can be applied on the medical device surface by any appropriate method. Preferred techniques include casting, spin coating, web coating, stereo-lithographic deposition, spraying, dipping, coating via air suspension and mechanical suspension techniques, positive displacement coating techniques, ink jet techniques, electrostatic techniques, and combinations of these processes. Spraying is a frequently used technique where coating retention is not of great concern (e.g., where the cost of the materials present in the crosslinking agent are relatively low).

The polymer-containing layer is subsequently deposited over the reactive layer. Preferably the cross-linkable polymer and the therapeutic agent are dissolved or dispersed in a carrier liquid, for example, water or an organic liquid. Because therapeutic agents are commonly handled in aqueous solutions, water is commonly preferred.

The polymer-containing layer can be applied over the reactive layer by any appropriate method, include the techniques set forth above. As previously noted, therapeutic agents are, in general, quite expensive. Hence, it is typically desirable to use techniques having high coating retention, of which stereolithographic deposition is one example.

Stereo-lithographic deposition (SLD) is a process by which material can be applied onto a surface to obtain a 3-dimentional structure. This structure can be created through repetitive layering of the coating material. In the case of small medical devices, such as endoluminal stents, SLD can provide the means for building a therapeutic coating in a specific location.

Referring now to FIG. 1, for example, a stent element 12 is illustrated, to which a reactive layer (not separately illustrated) has previously been applied. A nozzle 14 dispenses the polymer-containing layer 16 over the stent element 12, precisely directing the deposition location of the polymer-containing layer 16. After deposition, the polymer within the polymer-containing layer 16 reacts with the crosslinking agent that is present on the surface to form therapeutic-agent-containing crosslinked polymer network. Upon drying, the crosslinked network is securely attached to the stent surface. The resulting crosslinked network is preferably sufficiently durable to withstand stent crimping and expansion.

One illustrative analog of SLD would be writing on a radiator grill with a tube of toothpaste. The nozzle of the toothpaste tube allows one to control the lay of the bead of toothpaste. Pressure on the tube and the distance of the nozzle from the grill surface can control the thickness of the bead. Sometimes, the viscosity of the SLD coating material is high enough to facilitate such a toothpaste analogy. However, this is not always the case. Nonetheless, in the event that a low viscosity polymer-containing layer is deposited using the SLD process, the process of the present invention will render the polymer-containing layer more viscous upon contacting the surface due to the crosslinking that subsequently occurs, improving coating retention.

Moreover, as indicated above, the reactive layer generally presents a relatively hydrophilic surface for the subsequently applied polymer-containing layer. Where an aqueous-based liquid is applied to create the polymer-containing layer, the presence of this hydrophilic surface further improves coating retention and uniformity.

Of course, other techniques other than SLD can be used to create the polymer-containing layer. One preferred technique, particularly where high coating retention is not required, is spray coating. As with SLD, coating thickness can be varied, for example, by modification of coating process parameters, including increasing spray flow rate, slowing movement between the substrate to be coated and the spray nozzle, providing repeated passes, and so forth.

"Therapeutic agents", "pharmaceutically active agents", "pharmaceutically active materials", "drugs" and other related terms may be used interchangeably herein and include genetic therapeutic agents, non-genetic therapeutic agents and cells.

Exemplary non-genetic therapeutic agents for the practice of the invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-mitotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; and (o) agents that interfere with endogenous vasoactive mechanisms.

Exemplary genetic therapeutic agents for the practice of the invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Some additional exemplary genetic therapeutic agents for the practice of the invention include DNA encoding for the following: cytokines such as colony stimulating factors (e.g., granulocyte-macrophage colony-stimulating factor), tumor necrosis factors (e.g., fas ligand) and interleukins (e.g., IL-10, an anti-inflammatory interleukin), as well as protease inhibitors, particularly serine protease inhibitors (e.g., SERP-1), tissue inhibiting metalloproteinases (e.g., TIMP-1, TIMP-2, TIMP-3, TIMP-4), monocyte chemoattractant proteins (e.g., MCP-1), protein kinase inhibitors including cyclin-dependent kinase inhibitors (e.g., p27, p21), endogenous and inducible nitric oxide synthase, CO-generating enzymes, such as hemoxygenases, which catalyze the oxidation of heme into the biologically active molecules iron biliverdin and CO (e.g., HOI-1), antiproliferative compounds, such as hKIS in a transdominant mutant peptide form, which are capable of interfering with the ability of endogenous hKIS to phosphorylate p27 thereby enhancing cell cycle arrest, as well as derivatives of the foregoing.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD), as well as other transfection enhancing agents.

Cells include cells of human origin (autologous or allogeneic), including stem cells, or from an animal source (xenogeneic), which can be genetically engineered if desired to deliver proteins of interest.

Numerous therapeutic agents, not necessarily exclusive of those listed above, have been identified as candidates for vascular treatment regimens, for example, as agents targeting restenosis. Such agents are appropriate for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, (cc) blood rheology modulators such as pentoxifylline, and (dd) endothelial-cell specific mitogens.

Several of the above and numerous additional therapeutic agents appropriate for the practice of the present invention are also disclosed in U.S. Pat. No. 5,733,925 assigned to NeoRx Corporation, the entire disclosure of which is incorporated by reference.

Therapeutic agents may be used singly or in combination.

A wide range of therapeutic agent loadings can be used in connection with the above polymeric coatings, with the amount of loading being readily determined by those of ordinary skill in the art and ultimately depending upon the condition to be treated, the nature of the therapeutic agent itself, the avenue by which the therapeutic-agent-loaded polymeric coating is administered to the intended subject, and so forth. The loaded polymeric coating will frequently comprise from 1% or less to 70 wt % or more therapeutic agent.

EXAMPLE

In this example, a cross-linking agent is applied to the surface of a stent. The therapeutic is then delivered to the stent surface within a polymer solution. When the polymer solution contacts the cross-linking agent on the surface of the stent, the polymer forms a gel, and the therapeutic is held in a crosslinked matrix on the surface of the stent.

The following materials are used: (a) 2.5% (w/w) sodium alginate polymer solution (aqueous), (b) 1.0% (w/w) calcium chloride solution (aqueous), (c) Boston Scientific Express™ 8 mm coronary stent, Boston Scientific, Natick Mass., USA, (d) 26 gauge hypodermic needle w/syringe, (e) stereoscopic light microscope, (f) stent spray coater, and (g) Teflon-coated mandrels.

Stents are initially spray coated with the $CaCl_2$ solution and allowed to dry for 3 hours at 37° C. Sodium Alginate solution is then loaded into hypodermic syringe using care to eliminate any bubbles in the syringe. Dried stents are loaded onto mandrels, and using the light microscope, the needle tip is moved into a position directly over a $CaCl_2$-coated stent strut. Gentle pressure is used to introduce the alginate solution from the needle to the stent surface. With reference to FIG. 1, and to assist in visualizing the procedure, the stent strut can be thought of as corresponding to numeral 12, the needle to numeral 14, and the alginate solution to numeral 16.

Subsequent to application of the alginate on the $CaCl_2$-coated stent surface, the sodium alginate, which is a yellowish color, turns a noticeable shade of green. There appears to be some volume loss (shrinking) of the alginate as it gels as well. Alginate gels anywhere that $CaCl_2$ is present, but it does not do so on bare metal. Scratching the surface with a needle after depositing the alginate reveals a gel-like substance. Prolonged exposure to the microscope lights appears to dry the alginate gel and create a crystalline surface.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method for providing a therapeutic-agent-containing medical device, said method comprising: (a) providing a reactive layer comprising a cross-linking agent on a medical device surface; and (b) applying a polymer-containing layer comprising a crosslinkable polymer and a therapeutic agent over said reactive layer, wherein said cross-linking agent interacts with said crosslinkable polymer to form a cross-linked polymeric region comprising said therapeutic agent, and wherein said polymer-containing layer does not comprise said cross-linking agent at the time said polymer-containing layer is applied over said reactive layer.

2. The method of claim 1, wherein said medical device is an implantable or insertable medical device.

3. The method of claim 1, wherein said medical device is selected from a catheter, a balloon, a cerebral aneurysm filler coil and an arterio-venous shunt.

4. The method of claim 1, wherein said medical device is a stent.

5. The method of claim 4, wherein said device is a vascular stent.

6. The method of claim 1, wherein said crosslinking agent is an ionic crosslinking agent.

7. The method of claim 6, wherein said crosslinking agent is a cationic crosslinking agent.

8. The method of claim 7, wherein said polymer is a monovalent poly-glycosamino-glycan polymer.

9. The method of claim 8, wherein said polymer is sodium alginate.

10. The method of claim 8, wherein said crosslinking agent comprises calcium cations.

11. The method of claim 1, wherein said crosslinking agent is a covalent crosslinking agent.

12. The method of claim 11, wherein said covalent crosslinking agent covalently bonds two amino acids.

13. The method of claim 1, wherein said polymer-containing layer further comprises water at the time of application.

14. The method of claim 1, wherein said polymer-containing layer is applied by spray coating.

15. The method of claim 1, wherein said therapeutic agent comprises protein.

16. The method of claim 1, wherein said therapeutic agent comprises whole cells.

17. The method of claim 16, wherein said therapeutic agent further comprises extracellular matrix components.

18. The method of claim 1, wherein said therapeutic agent comprises DNA.

19. The method of claim 18, wherein said therapeutic agent further comprises a vector for delivering said DNA.

20. The method of claim 19, wherein said vector is a viral vector.

21. The method of claim 1, wherein said medical device surface is a hydrophobic surface, wherein said reactive layer is provided on said hydrophobic surface in the form of an aqueous liquid comprising water and said cross-linking agent, and wherein said polymer-containing layer is applied on said reactive layer in the form an aqueous liquid comprising a polymer, a therapeutic agent and water.

22. The method of claim 1, wherein said medical device surface is a metallic surface, wherein said reactive layer is provided on said metallic surface in the form of an aqueous liquid comprising water and an ionic cross-linking agent, and wherein said polymer-containing layer is applied on said reactive layer in, the form an aqueous liquid comprising an ionically cross-linkable polymer, a therapeutic agent and water.

23. The method of claim 1, wherein said medical device surface is a metallic surface; wherein said reactive layer is provided on said metallic surface in the form of an aqueous liquid comprising water and a cationic cross-linking agent, and wherein said polymer-containing layer is applied on said reactive layer in the form an aqueous liquid comprising a cationically cross-linkable polymer, a therapeutic agent and water.

24. The method of claim 1, wherein the reactive layer provided prior to the application of the polymer-containing layer does not comprise a therapeutic agent.

25. The method of claim 1, wherein the reactive layer and the polymer-containing layer are sufficiently reactive with one another such that essentially all of the polymer within the polymer-containing layer is crosslinked by the crosslinking agent.

26. A method for providing a therapeutic-agent-containing medical device comprising: (a) providing a reactive layer comprising a cross-linking agent on a medical device surface; and (b) applying a polymer-containing layer consisting essentially of a polymer and a therapeutic agent over said reactive layer, wherein said cross-linking agent interacts with said polymer to form a cross-linked polymeric region comprising said therapeutic agent.

* * * * *

UNITED STATES PATENT AND TRADEMARK OFFICE
CERTIFICATE OF CORRECTION

PATENT NO. : 7,390,525 B2  Page 1 of 1
APPLICATION NO. : 11/033918
DATED : June 24, 2008
INVENTOR(S) : Epstein et al.

It is certified that error appears in the above-identified patent and that said Letters Patent is hereby corrected as shown below:

In the Abstract item [56], Line 13, after "catheters", change "balloon," to -- balloons, --.
Specification, Col. 1, Line 44, before "medical", change "therapeutic agent releasing", to -- therapeutic-agent-releasing --.
Specification, Col. 1, Line 45, after "According", insert -- to --.
Specification, Col. 1, Line 60, before "polymer", change "therapeutic-containing" to -- therapeutic-agent-containing --.
Specification, Col. 2, Line 59, after "refers", insert -- to --.
Specification, Col. 2, Line 62, after "elimination", insert -- of --.
Specification, Col. 4, Line 39, after "groups" (first occurrence), insert -- , --.
Specification, Col. 5, Line 11, after "method,", change "include" to -- including --.
Specification, Col. 5, Line 18, before "structure," change "3-dimentional" to -- 3-dimensional --.
Specification, Col. 5, Line 30, after "form", insert -- a --.
Specification, Col. 9, Line 4, after "therapeutic", insert -- agent --.
Specification, Col. 9, Line 7, after "therapeutic", insert -- agent --.
Specification, Col. 9, Line 18, after "into", insert -- a --.
Claim 5, Col. 9, Line 61, after "said", insert -- medical --.
Claim 21, Col. 10, Line 32, after "form", insert -- of --.
Claim 22, Col. 10, Line 39, after "form", insert -- of --.
Claim 22, Col. 10, Line 39, after "layer", change "in," to -- in --.
Claim 23, Col. 10, Line 47, after "form", insert -- of --.

Signed and Sealed this

Seventeenth Day of February, 2009

JOHN DOLL
*Acting Director of the United States Patent and Trademark Office*